(12) United States Patent
Partain et al.

(10) Patent No.: US 7,492,858 B2
(45) Date of Patent: Feb. 17, 2009

(54) SYSTEM AND METHOD FOR IMAGING AND TREATMENT OF TUMOROUS TISSUE IN BREASTS USING COMPUTED TOMOGRAPHY AND RADIOTHERAPY

(75) Inventors: Larry D. Partain, Los Altos, CA (US); David H. Humber, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 54 days.

(21) Appl. No.: 11/134,695

(22) Filed: May 20, 2005

(65) Prior Publication Data

US 2006/0262898 A1 Nov. 23, 2006

(51) Int. Cl.
*A61B 6/03* (2006.01)
*A61B 6/04* (2006.01)

(52) U.S. Cl. .................. 378/37; 378/20; 378/196; 378/209; 5/601

(58) Field of Classification Search ............ 378/20, 378/37, 64, 65, 68, 203, 208, 209, 177, 195, 378/196, 197; 5/601; 128/845; 250/492.3, 250/515.1, 516.1, 519.1
See application file for complete search history.

(56) References Cited

U.S. PATENT DOCUMENTS

| 3,165,630 | A | * | 1/1965 | Bielat et al. ............ 378/37 |
|---|---|---|---|---|
| 3,973,126 | A | * | 8/1976 | Redington et al. ........ 378/17 |
| 4,938,233 | A | * | 7/1990 | Orrison, Jr. ............. 128/849 |
| 5,078,142 | A | * | 1/1992 | Siczek et al. ............ 600/407 |
| 5,233,990 | A | * | 8/1993 | Barnea ................... 600/427 |
| 5,289,520 | A | * | 2/1994 | Pellegrino et al. ........ 378/37 |
| 5,308,321 | A | * | 5/1994 | Castro ................... 600/415 |
| 5,386,447 | A | * | 1/1995 | Siczek ................... 378/37 |
| 5,564,438 | A | * | 10/1996 | Merchant ................ 5/613 |

(Continued)

FOREIGN PATENT DOCUMENTS

WO WO 2006/119426 A2 11/2006

(Continued)

OTHER PUBLICATIONS

Boone, J. M. et al., A comprehensive analysis of $DgN_{CT}$ coefficients for pendant-geometry cone-beam breast computed tomography, *Med Phys* vol. 31, No. 2, Feb. 2004, pp. 226-235.

(Continued)

*Primary Examiner*—Allen C. Ho
(74) *Attorney, Agent, or Firm*—Houst Consulting

(57) ABSTRACT

The present invention provides a system 10 for irradiating a breast 20 of a patient 22. The system 10 comprises a gantry 12 rotatable about a horizontal axis 14 and comprising a radiation source 16 for generating a radiation beam 18 and a detector 24 spaced from the radiation source 16, and a barrier 26 disposed between the patient 22 and the gantry 12. The barrier 26 is provided with an opening 30 adapted to allow a breast 20 passing therethrough to be exposed to the radiation beam 18. In some embodiments, the barrier 26 is provided with an opening 30 adapted to allow both the breast 20 and the tissue leading from the breast to axilla and the muscle tissue of the adjacent chest wall passing therethrough to be exposed to the radiation beam 18.

46 Claims, 9 Drawing Sheets

U.S. PATENT DOCUMENTS

| | | | |
|---|---|---|---|
| 5,751,781 A * | 5/1998 | Brown et al. | 378/65 |
| 5,820,552 A * | 10/1998 | Crosby et al. | 378/37 |
| 5,999,587 A | 12/1999 | Ning et al. | |
| 6,075,836 A | 6/2000 | Ning | |
| 6,125,295 A * | 9/2000 | Cash et al. | 600/431 |
| 6,146,377 A * | 11/2000 | Lee et al. | 606/13 |
| 6,254,538 B1 * | 7/2001 | Downey et al. | 600/439 |
| 6,254,614 B1 * | 7/2001 | Jesseph | 606/130 |
| 6,275,564 B1 * | 8/2001 | Ein-Gal | 378/68 |
| 6,298,110 B1 | 10/2001 | Ning | |
| 6,298,114 B1 * | 10/2001 | Yoda | 378/37 |
| 6,378,149 B1 * | 4/2002 | Sanders et al. | 5/624 |
| 6,419,390 B1 * | 7/2002 | Landis-Lowell | 378/209 |
| 6,446,286 B1 * | 9/2002 | Karmalawy | 5/601 |
| 6,459,762 B1 * | 10/2002 | Wong et al. | 378/65 |
| 6,463,122 B1 * | 10/2002 | Moore | 378/65 |
| 6,477,221 B1 | 11/2002 | Ning | |
| 6,480,565 B1 | 11/2002 | Ning | |
| 6,504,892 B1 | 1/2003 | Ning | |
| 6,577,702 B1 * | 6/2003 | Lebovic et al. | 378/37 |
| 6,618,466 B1 | 9/2003 | Ning | |
| 6,842,502 B2 * | 1/2005 | Jaffray et al. | 378/65 |
| 6,865,254 B2 * | 3/2005 | Nafstadius | 378/65 |
| 6,883,194 B2 * | 4/2005 | Corbeil et al. | 5/601 |
| 6,922,859 B2 * | 8/2005 | Gagnon et al. | 5/601 |
| 6,987,831 B2 * | 1/2006 | Ning | 378/37 |
| 2002/0154727 A1 | 10/2002 | Ning | |
| 2003/0099328 A1 | 5/2003 | Jensen et al. | |
| 2004/0081273 A1 | 4/2004 | Ning | |
| 2005/0143638 A1 * | 6/2005 | Johnson et al. | 600/407 |
| 2006/0094950 A1 | 5/2006 | Ning | |

FOREIGN PATENT DOCUMENTS

WO    WO 2006/119426 A3    11/2006

OTHER PUBLICATIONS

Formenti, Silvia C. et al., Prone accelerated partial breast irradiation after breast-conserving surgery: preliminary clinical results and dose-volume histogram analysis, *Int. J. Radiation Oncology Biol. Phys.*, vol. 60, No. 2, 2004, pp. 493-504.

C.H.Chang et al, "Computed Tomography of the Breast", *Radiology*, (1977) 124:827-829.

J.J. Gisvold et al, "Clinical Evaluation of Computerized Tomographic Mammography", *Mayo Clin Proc*, (1977) 52:181-185.

J.J. Gisvold et al, "Computerized Tomographic Mammography", *W.W.Logan Ed.* (1977) 219-238.

J.J. Gisvold et al, "Computerized Tomographic Mammography", CTM Mayo Clinic (1977), 2 pages.

* cited by examiner

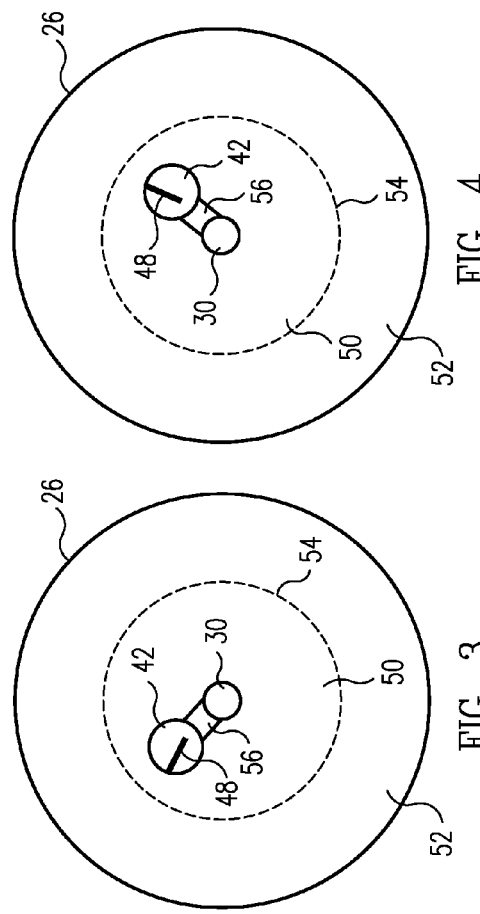
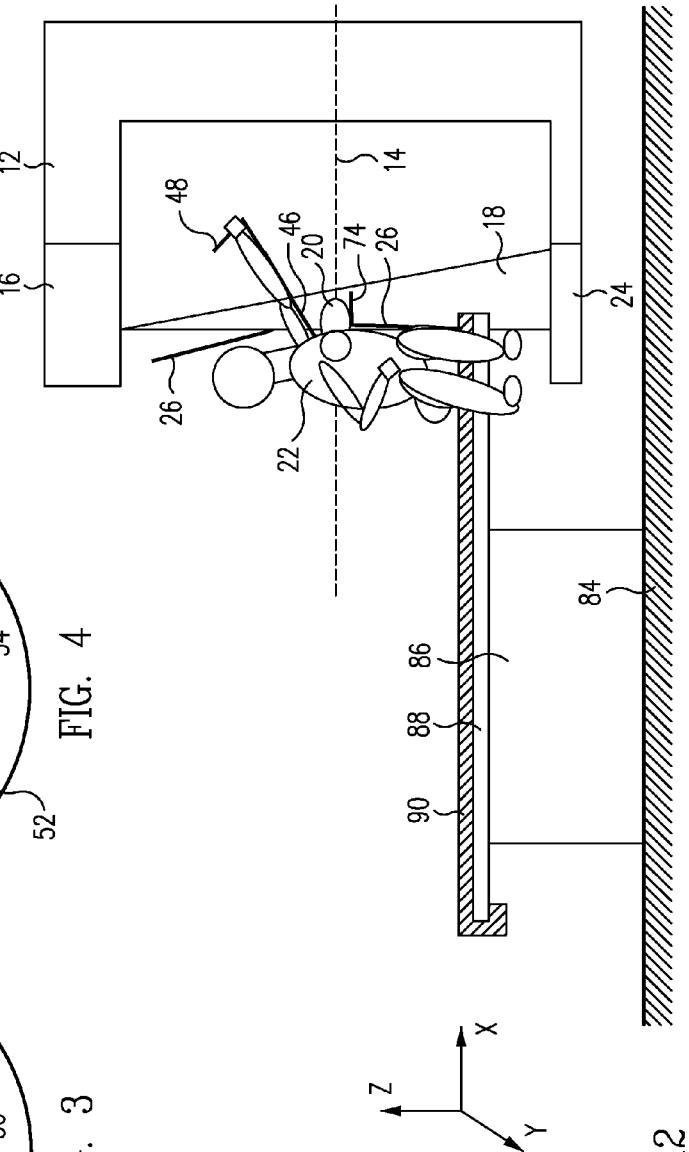

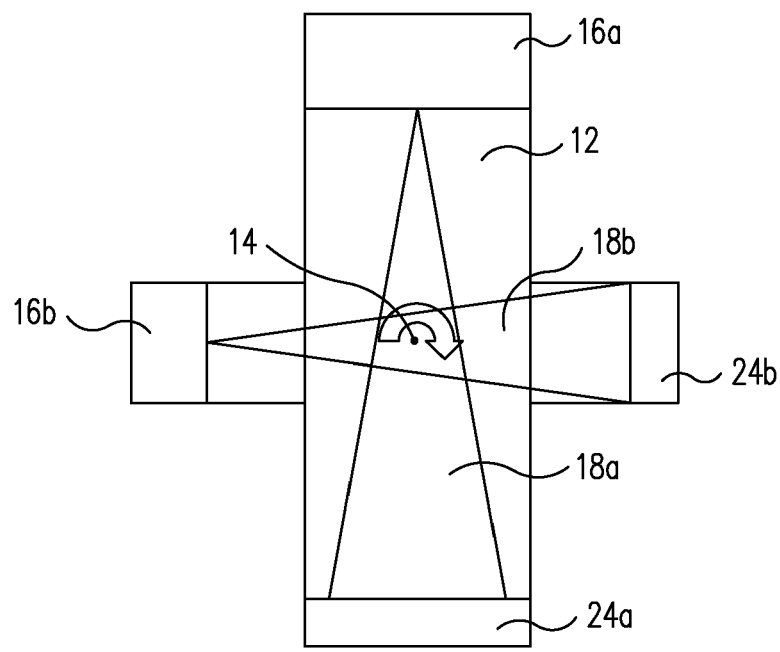
FIG. 5
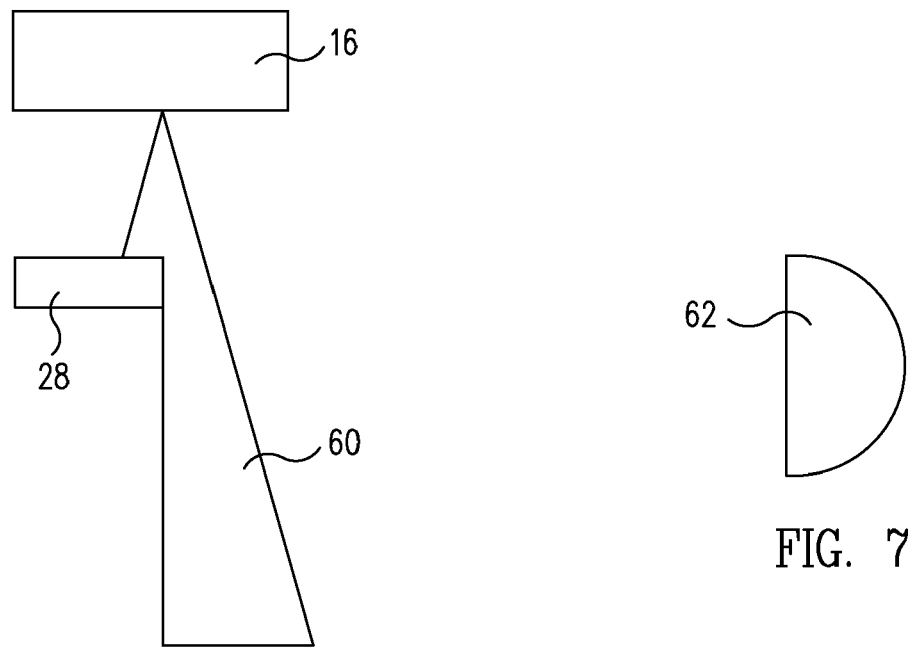
FIG. 6
FIG. 7

SYSTEM AND METHOD FOR IMAGING AND TREATMENT OF TUMOROUS TISSUE IN BREASTS USING COMPUTED TOMOGRAPHY AND RADIOTHERAPY

FIELD OF THE INVENTION

This invention relates generally to a system and method of providing radiation imaging and/or treatment and in particular, to a system and method for imaging and treatment of tumorous tissue in breasts using computed tomography (CT) and radiotherapy.

BACKGROUND

Radiological evaluation of breasts is important not only for early detection of disease in breasts, but also for staging, treatment targeting and monitoring responses to treatment. Conventional x-ray mammography has been shown a cost-effective tool for early detection of breast cancer. In conventional x-ray mammography, a breast is positioned on a platform and compressed with plastic plates. The breast is compressed in order to even out the breast thickness so that the correct dose of X-rays can be delivered for clear images without over exposure in thinner regions and under exposure in thicker regions and also to spread out the tissue to reduce the likelihood of obscuring benign and malignant lesions at different tissue levels. Two images of the breast, medio-lateral oblique (MLO) and cranio-caudal (CC), are typically made at an oblique angle to each other to increase the likelihood of seeing features in the breast that are not recognizable from one direction, but which may be discernable in another direction.

The predictive value and specificity of x-ray mammography remain limited however, due to projecting a three-dimensional object into a two-dimensional image and due to poor contrast detectability. Incorrectly diagnosing malignant tissue as healthy can result in missing cancers in their early stages while incorrectly diagnosing healthy tissue as malignant can lead to unnecessary surgical procedures. In indeterminate cases, biopsy is often necessary, despite the disadvantages of high cost and the stress imposed on patients.

Cone beam CT systems have been used to provide three-dimensional images of uncompressed breasts of patients. In cone beam CT, a patient lies in a prone position on a couch having a hole in it. The patient's breast extends down through this hole and a cone beam CT machine rotates around it about a vertical axis of rotation. This system has minimal radiation dose to the rest of the patient's body (including the heart and lungs) since only the breast itself is exposed to the radiation beam. One limitation of this type of system is that it only images the breast itself without providing image information on the important soft tissue between the breast and the axilla (arm pit) where primary breast lesions often spread to infect lymph nodes in this region. Another limitation is that it cannot make immediate use of widely available CT gantry systems and external beam radiotherapy systems, which primarily have axes of rotation that are horizontal.

Spiral CT scanners have been used to produce images of breasts and surrounding tissues. In spiral CT, a patient lies on a couch, which is moved into a gantry where a radiation source rotates many revolutions about a horizontal axis of rotation to produce the spiral. Since the radiation source is always pointed directly at the patient as it moves around, all the tissue of the chest adjacent to the breasts is exposed to the radiation beam from multiple directions to produce continuous flow of images in relative short period of time. One limitation of this type of system is that it scans not only the target breast and surrounding soft tissue, but also simultaneously exposes the heart, lungs and other body parts to unnecessary radiation.

Accordingly, there is a need for an improved system and method for computed tomography of breasts and radiotherapy of tumorous tissues in breasts.

SUMMARY OF THE INVENTION

The present invention provides a system and a method useful in cone beam computed tomography and radiotherapy. In some embodiments, the present invention provides a structure for use in irradiating a portion of a body in a gantry. The structure is adapted to be positioned between the body and at least a portion of a radiation beam and provided with an opening adapted to allow a portion of the body passing therethrough to be exposed to the radiation beam. The structure can perform one or more functions of a radiation barrier, a physical barrier, a support, a positioning device and an immobilization device for use in irradiating, for example, a breast of a patient in a gantry. In some embodiments, the structure is in the form of a barrier. In the present specification, numerous embodiments are illustrated with a structure referred to as a barrier, which may function, for example, as a barrier to radiation or a barrier between a patient area and moving parts of the equipment. It will be appreciated that in each of these embodiments, if desired the structure may or may not comprise a barrier and may or may not perform different or additional functions. The barrier can be positioned between the patient and the gantry so that the patient can rest against it and is supported. In some embodiments, the barrier comprises a material that absorbs the non-breast-irradiating part of the radiation beam to protect the healthy parts of the body from unnecessary irradiation. In some embodiments, the barrier functions to physically prevent collision between any parts of the patient's anatomy with moving parts of the gantry. The barrier is provided with an opening adapted to allow a breast passing therethrough to be exposed to the radiation beam. In some embodiments, the barrier is provided with an opening adapted to allow both the breast and the axillary extension of the breast to be exposed to the radiation beam. As used herein, an axillary extension of a breast refers to any soft tissues leading from the breast to the axilla or armpit. In several embodiments, an opening for e.g. a breast and an opening for e.g. an arm are described. It will be appreciated that as used herein, such description may comprise a single opening adapted to allow both to pass through. Thus, for example, a first opening and a second opening as used herein may refer to a single opening as well as to a plurality of openings.

In some embodiments, a holder can be attached to the barrier for supporting the breast. The holder can be a hollow cylinder and comprise an end cap that is removable to facilitate positioning of the breast in the holder. The hollow cylinder can be provided with a vacuum line for evacuating the holder so that the breast can be more completely drawn into and stabilized in the hollow cylinder. A soft gasket can be provided to vacuum seal the breast in the cylinder.

In some embodiments, the barrier is provided with a plurality of holes surrounding the opening area for preventing formation of vacuum in a region beyond the breast.

In some embodiments, the holder is an open ledge that supports the breast from below with no vacuum environment. This support ledge can be a simple flat surface oriented horizontally or at some small angle (e.g. 5 to 30 degrees) to the horizontal. In some embodiments, this open ledge has the curved shape of a half cup. In some embodiments, this ledge is a combination of flat and curved surfaces. In some embodiments the breast support is a flexible material that provides positioning and immobilization much like that of a brassiere.

The barrier can be in the shape of a cone, partial spheroid, many faceted pyramid or any arbitrary combination of flat and/or curved surfaces that support and/or protect the patient while allowing proper X-ray exposure of the breast and its axillary extension from the moving gantry. In some embodiments, the barrier can comprise an inner section and an outer section. The inner section is detachable from the outer section and provided with the opening adapted to allow a patient's breast and arm passing therethrough. In some embodiments, the inner section is rotatable with respect to the outer section such that the location of the opening in the barrier is changeable.

In another aspect, the present invention provides a method of irradiating a patient's breast. In an embodiment, a barrier is provided between a patient and a gantry. The gantry includes a radiation source for generating a radiation beam and a detector spaced from the radiation source. The patient is positioned in a substantially upright position. The patient's breast is then extended through an opening in the barrier to be exposed to the radiation beam. The gantry rotates about a horizontal axis, whereby the breast is irradiated by the radiation beam and detected by the detector.

In some embodiments, the method further comprises the step of extending the tissue leading from the breast to axilla through an opening in the barrier. In some embodiments, the method further comprises the step of extending an arm of the patient through an opening in the barrier.

In some embodiments, the radiation barrier can be provided with three openings adapted to allow either the left or right arm of a patient passing therethrough either of two of the three openings, as either the left or right breast, respectively, passes through the third opening, so that either breast can be irradiated sequentially without modification of the barrier.

In a further aspect, the present invention provides a system for irradiating a patient's breast. The system comprises a gantry which comprises a radiation source for generating a radiation beam and a detector spaced from the radiation source, and a barrier disposed between the patient and the gantry. The barrier can comprise a material that absorbs the part of the radiation beam that is not incident on the breast and related tissue and is provided with an opening adapted to allow a breast passing therethrough to be exposed to the radiation beam. In some embodiments, the barrier is provided with an opening adapted to allow both the breast and the tissue leading from the breast to axilla passing therethrough to be exposed to the radiation beam. In some embodiments, the barrier comprises an opening adapted to allow an arm of the patient passing therethrough.

The system can comprise a holder for supporting the breast. The holder can be substantially cylindrical and comprise an end cap that is removable to facilitate positioning of the breast in the holder. The holder can comprise a gasket for vacuum sealing the breast in the holder. The holder can also be provided with means for providing vacuum to facilitate positioning and stabilizing of the breast in the holder. The system can further comprise a panic button coupled to the vacuum means, which when pushed, turns off the vacuum in the holder.

In some embodiments, the system can comprise a radiation source generating a cone x-ray beam in a keV energy level suitable for diagnostic imaging. In some embodiments, the system can comprise a radiation source generating a cone x-ray beam in a MeV energy level suitable for therapeutic irradiation. The system can further comprise a collimator for producing a radiation beam having a sharp vertical edge and semi-circular cross-section.

In some embodiments, the gantry can comprise a first radiation source for generating a first radiation beam suitable for diagnostic imaging and a second radiation source for generating a second radiation beam suitable for therapeutic imaging and/or treatment. The first and second radiation sources can be attached to a common gantry. Alternatively, the first radiation source is attached to a first gantry, the second radiation source is attached to a second gantry, and the first and second gantries are rotatable about a common axis.

In some embodiments, the patient lies prone onto a barrier layer that is substantially horizontal in orientation, the breast hangs down through a hole in the barrier, and the gantry rotates about a vertical axis. A slot is provided in the barrier and a cylinder is attached to the barrier in such a way that the arm nearest the breast extends down by and past the breast in a way that allows clear X-ray exposure of the breast and its axillary extension and the chest wall without exposing the heart and lungs and so that no collision occur between body parts and the rotating gantry. Special rotation sequences and trajectories may be used to minimize the X-ray dose exposure to the arm and shoulder tissues and bones, from this arm insertion.

In some embodiments, the patient's head-to-foot orientation can be in any plane from vertical to horizontal, or stated alternatively, the angle between patient's head-to-foot orientation and a vertical axis can be at any desired angle.

In one embodiment, the system may include a couch top moveable relative to the gantry and a support attachment coupled to the couch top. The patient may lie down on her side on the support attachment during imaging. The support attachment may comprise a drop-down or raise-up portion adapted to patient's built. In an embodiment, the attachment is moveable in three directions (x, y, and z). In another embodiment, the attachment is moveable independent of the couch top. In a further embodiment, the attachment may include a central portion and two wing portions, each of which being adapted to support the patient in a lying position. In some embodiments, each of the two wing portions is attachable and/or foldable.

For radiation therapy treatment, one embodiment has both a kilovoltage x-ray source and flat plate detector and a megavoltage x-ray source and detector, mounted at 90 degrees to each other on a single rotating gantry. In one particular embodiment, the kilovoltage source is placed near the outside boundary edge of the gantry volume in the direction of the patient. The latter permits the minimum bending of patient anatomy, such as the neck, to allow imaging of important areas, such as the muscle wall of the chest, with minimal exposure of sensitive healthy regions, like the head and neck. The megavoltage x-ray source can be located in a more central part of the gantry volume that is not conducive to the same boundary edge beam locations as a kilovoltage source. The gantry can also be positioned to several (e.g., 2 to 8) specific angles and orientations, to deliver a prescribed megavoltage dose to the breast, or to a restricted volume in the breast, without a large dose being delivered to other sensitive areas, such as the head, neck, heart and lungs. With the embodiment discussed here, the location, extent, shape, orientation and/or boundaries of the malignant tumor are precisely determined in 3 dimensional space, relative to the gantry system coordinates, by the kilovoltage source and detector's acquisition of a cone beam CT data set. These data are analyzed to either compare these specifications to a preexisting treatment plan or to produce a new or a modified treatment plan. Then the desired dose, to the whole breast and/or to its axillary extension and/or to its adjacent chest wall muscle, or to a restricted volume containing the malignant tumor, is then accurately delivered by the megavoltage source, monitored by the flat panel megavoltage sensor, all on the single gantry and all during short time span (less than 30 minutes) for a single dose delivery. Since megavoltage x-ray beam radiotherapy is routinely administered in many separate daily doses, called fractions, over many weeks, this embodiment allows some determination of the tumor's response to treatment. This response can be indicated by comparisons to earlier fractions, as evident by changes in location, extent, shape, orientation, boundaries, or by detection of contrast agents related to functional, biological and/or structural characteristics, where these agents are administered as part of the treatment setup and delivery, and as evaluated by cone beam CT data set viewing and analysis procedures. These 3 dimensional data sets can be extended to the $4^{th}$ dimension time by using respiratory gating during cone beam CT acquisition to correlate position with the phase of the patients breathing process.

For some embodiments, the barrier is adapted to incorporate a ring ledge that allows the patient to be positioned further inside the rotating gantry so that the shaped x-ray beam and/or beams strike the breast, and/or its axillary extension and/or its chest wall section of the patient, without the need to move the x-ray source and/or sources, to the outside perimeter of the housings, but remain in the central region of the source enclosure, as is characteristic of most standard rotating C-arm x-ray sources and imager panels.

BRIEF DESCRIPTION OF THE DRAWINGS

These and various other features and advantages of the present invention will become better understood upon reading of the following detailed description in conjunction with the accompanying drawings and the appended claims provided below, where:

FIG. 3 is a plane view of a barrier having openings therein in accordance with an embodiment of the present invention;

FIG. 4 is a plane view of a barrier having openings therein in accordance with an embodiment of the present invention;

FIG. 5 schematically illustrates two radiation beams generated from two radiation sources arranged at 90 degrees in accordance with an embodiment of the present invention;

FIG. 6 schematically illustrates a radiation source and a collimator for producing a radiation beam in accordance with an embodiment of the present invention;

FIG. 7 is a cross-sectional view of a radiation beam produced by the radiation source and collimator illustrated in FIG. 6;

FIG. 12 schematically illustrates a radiation system including a barrier coupled to a moveable couch top in accordance with an embodiment of the present invention;

DETAILED DESCRIPTION OF THE INVENTION

Referring to FIGS. 1 to 18, where like elements are designated by like references, various exemplary embodiments of the radiation system and method of the present invention will now be described. In general, the radiation system includes a gantry comprising a radiation source for generating a radiation beam to irradiate a portion of a body, a detector spaced from the radiation source, and a structure positioned between the body and the gantry. In the present specification, the invention is described with embodiments where a human breast is irradiated, for example, for the purpose of forming an image thereof. It will be appreciated that the claimed invention may be used on animals as well as humans, and may be used on different body parts. The structure is described in the illustrative embodiments as a protective barrier that prevents at least a portion of the radiation from reaching other portions of the body, but can perform different or additional functions. For example, the structure can perform one or more functions such as: radiation barrier, patient support, patient positioning, patient immobilization, and patient protection from moving parts, for example.

Figure 1:
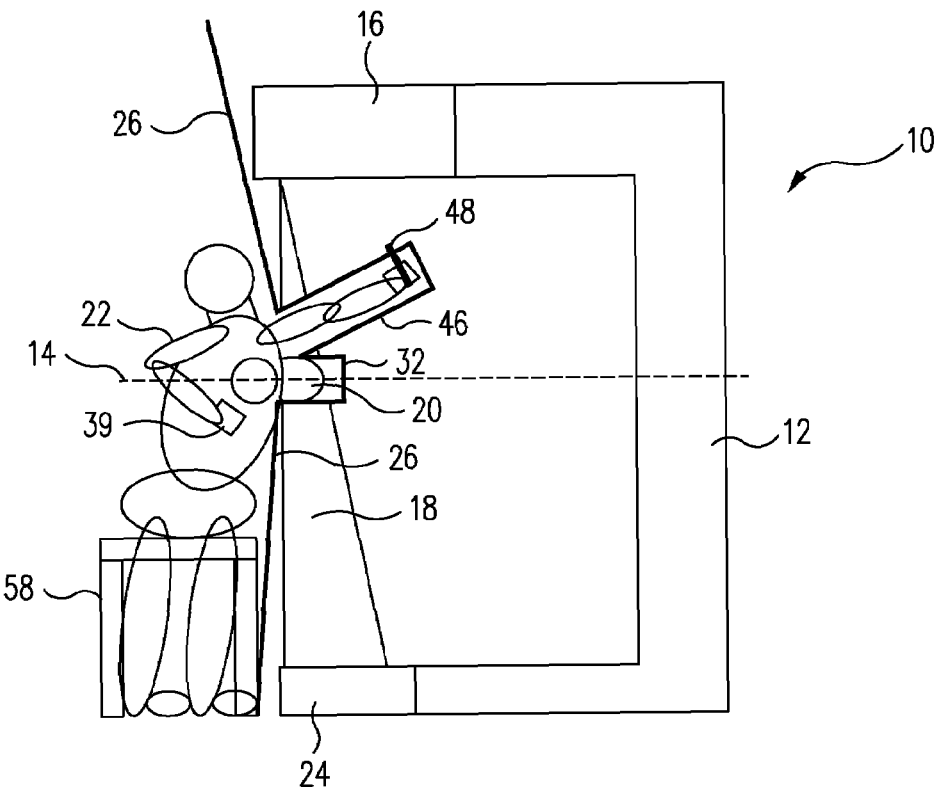
FIG. 1 schematically illustrates a radiation system including a barrier between a patient and a gantry in accordance with an embodiment of the present invention.

FIG. 1 schematically illustrates a radiation system 10 in accordance with a specific embodiment of the present invention. Radiation system 10 includes a gantry 12 capable of rotating about a horizontal axis 14. Gantry 12 includes a radiation source 16 for generating a radiation beam 18 for irradiating a breast 20 of a patient 22, and a detector 24 spaced from radiation source 16 for detecting the radiation beam transmitted through breast 20. A barrier 26 is positioned between patient 22 and gantry 12.

Radiation source 16 is capable of generating radiation beams at different energy levels. Radiation source 16 may include a single beam generation module or multiple beam generation modules (not shown). In accordance with a specific embodiment of the present invention, radiation source 16 is configured to generate x-ray radiation beams at a kiloelectron-volt (keV) energy level and a mega-electron-volt (MeV) energy level. A keV energy level x-ray radiation beam is generally used for forming images of tumor and/or tissues in patient, and is therefore also referred to as an image beam or a diagnostic beam. A MeV energy level x-ray radiation beam is generally used for targeting and treating tumor or other abnormal tissue in patient. The MeV energy level x-ray radiation beam can also be used for forming images of patient. However, images formed using an MeV energy level x-ray beam typically have lower contrast and spatial resolutions than those formed with an x-ray beam at a lower energy level, e.g., keV energy level. The MeV energy levels have the advantage that they reduce CT image artifacts, like rings and rays, generated by dense regions of patient anatomy, like bones and metal implants. In accordance with an embodiment of the present invention, radiation source 16 includes two x-ray beam generators 16a and 16b (FIG. 5), one for generating the keV energy level x-ray image beams and another for generating the MeV energy level x-ray radiation beams. The two beam generators may be located in close proximity with each other or separated from each other. For example, in one specific embodiment, the two beam generators are so located that they project radiation beams toward the breast at an angle of approximately 90 degree from each other. In accordance with another embodiment, radiation source 16 includes a signal x-ray beam generator that is capable of generating x-ray beams at multiple energy levels. An embodiment uses dual (e.g. keV and MeV) energies to provide additional medically relevant information. For example, by use of dual energy techniques that include projection image subtractions or ratioing, or other simple or complex (e.g. correlation and mutual information) mathematical operations on the dual energy data well known in the art, including such operations as a function of time, embodiments provide increased sensitivity, to elements like contrast agents, and evaluations of functional performance parameters, such as perfusion and cellularity. By way of example, U.S. patent application Ser. No. 10/033,327 entitled "Radiotherapy Apparatus Equipped with an Articulable Gantry for Positioning an Imaging Unit" and filed on Nov. 2, 2001, now U.S. Pat. No. 6,888,919, discloses a system with x-ray radiation sources at different energy levels, the disclosure of which is incorporated herein by reference in its entirety.

A beam adjuster 28 (FIG. 6) may be included in gantry 12 in front of radiation source 16 to adjust the shape, size, intensity, and direction of radiation beam 18. In a specific embodiment, beam adjuster 28 includes one or more multiple leaf collimators. In an alternative embodiment, beam adjuster 28 includes one or more multiple leaf collimators and one or more single jaw collimators.

Detector 24 is capable of detecting images of tumor and surrounding tissues in patient formed by x-ray beams at both the MeV high energy level and the keV low energy level. In accordance with an embodiment, detector 24 includes two image detecting devices 24a and 24b (FIG. 5), one for detecting images formed by the keV image beams, and the other for detecting images formed by the MeV radiation beams. In accordance with another embodiment, detector 24 includes a single image detecting device that is capable of detecting images formed by beams at multiple energy levels. By way of example, U.S. patent application Ser. No. 10/013,199 entitled "X-Ray Image Acquisition Apparatus" and filed on Nov. 2, 2001, now U.S. Pat. No. 6,800,858, discloses an x-ray image detecting device that is capable of detecting multiple energy level x-ray images and can be used as detector in accordance with the present invention. U.S. patent application Ser. No. 10/013,199 is incorporated herein by reference in its entirety.

In accordance with a specific embodiment of the present invention, detector 24 is a flat plate x-ray sensor.

System 10 can include a control module (not shown) coupled to gantry 12, radiation source 16, beam adjuster 28, and detector 24 to control their operations.

It should be noted that system 10 in accordance with the present invention is not limited to having the structure as described herein above. For example, radiation source 16 is not limited to generating x-ray radiation at the keV and MeV energy levels. Depending on the nature of treatment or application, radiation source 16 may generate x-ray radiation at other energy levels or generate other kinds of radiation beams, which include, but are not limited to, beta ray beams, positron beams, proton beams, antiproton beams, neutron beams, heavy ion beams, e.g., alpha ray beams, carbon ion beams, etc. Detector 24 may include different kinds of radiation sensors corresponding to different radiation beam sources. Further, system 10 is not limited to having one detector as shown in FIG. 1. In alternative embodiments, system may include two or more image detectors.

Barrier 26 is positioned between patient 22 and gantry 12 to protect the rest of the patient's body from radiation. Barrier 26 can also perform the functions of supporting patient 22 for correct and stable position and protecting patient 22 from collision with moving gantry 12. Barrier 26 can be mounted on the ceiling and the floor of the treatment room in which system 10 is installed. Barrier 26 can be in various forms and sizes depending on specific applications. By way of example, FIGS. 1-4 show a barrier in the form of a shallow cone having circular symmetry for illustration purpose. Other alternative embodiments include shallow partial spheroids, curved shapes, or shallow pyramids formed by multiple planar surfaces. Alternatively, barrier 26 can be formed by a combination of curved and planar surfaces. FIGS. 8-13 show alternative embodiments of barrier 26, which will be described in more detail below.

In some embodiments, barrier 26 comprises materials that absorb radiation such as x-ray beam 18. Suitable radiation absorbing materials are well known in the art, which include, but are not limited to: lead, tungsten, tantalum, uranium, thorium, iridium, gold, and their alloys or mixtures or in binders that contain them including glass, plastic, and sheet rock. In a specific embodiment, barrier 26 is formed of leaded sheet rock. Near the region of the patient's breast 20, barrier 26 can include a material that has a low absorption of radiation beam 18 to allow free penetration to areas of interest such as the chest wall of the patient.

Figure 2:
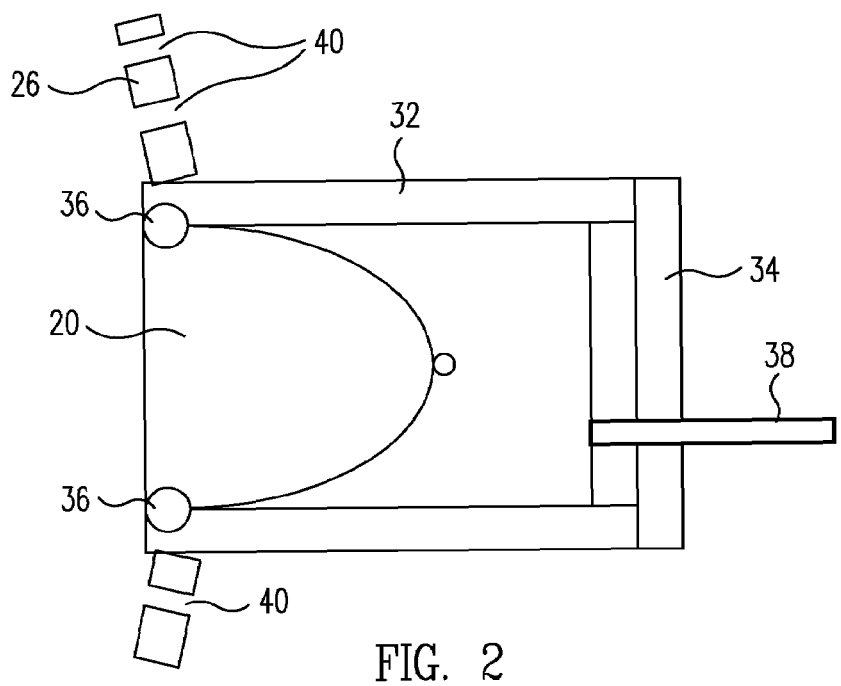
FIG. 2 schematically illustrates an uncompressed breast extended through an opening in a barrier and supported in a holder in accordance with an embodiment of the present invention.

Barrier 26 is provided with an opening 30 (FIGS. 3 and 4) adapted to allow a breast 20 and chest wall passing therethrough to be exposed to radiation beam 18. FIG. 2 schematically shows the detail of an uncompressed breast 20 extended through opening 30 in barrier 26. As shown in FIG. 2, a holder 32 is coupled to barrier 26 for receiving and supporting uncompressed breast 20. By way of example, holder 32 can be a hollow cylinder having an end cap 34. End cap 34 can be removable to allow a radiation technician to place and position breast 20 in hollow cylinder 32. A soft gasket 36 can be attached to hollow cylinder 32 to provide vacuum seal near the chest wall boundaries of breast 20. A vacuum line 38 can be coupled to hollow cylinder 32 for evacuating the cylinder. Vacuum line 38 allows breast 20 to be more completely drawn into and stabilized in hollow cylinder 32 and into radiation beam 18. Both holder 32 and gasket 36 can be made of a material that has a low absorption of x-ray beam so that clear imaging of breast anatomy is not compromised. A panic button 39 can be provided in barrier 26 or held in a free hand of patient 22. When the panic button is pushed, the vacuum in hollow cylinder 32 is turned off so that patient 22 has control of releasing herself from breast support cylinder 32 at any time. A plurality of small holes 40 can be provided in the area proximate opening 30 to prevent formation of vacuum beyond the immediate region of breast 20.

Barrier 26 can be provided with another opening 42 (FIGS. 3 and 4) adapted to allow an arm of patient 26 passing therethrough. A cylindrical support 32 is coupled to barrier 26 for receiving and supporting the extended arm. A hand bar 48 can be provided e.g. at one end of cylindrical support 46 to assist patient 22 to hold and stabilize the extended arm. Cylindrical support 46 can be made of the same material as that of barrier 26. Alternatively, cylindrical support 46 is made of a different material. In some embodiments, cylindrical support 46 comprises a material that absorbs radiation beam 18 such as x-ray beams. In some embodiments, near the region of patient's chest wall and breast, cylindrical support 46 comprises a material that has low absorption of radiation so that radiation beam 18 passes through for clear imaging of the chest wall, the breast and its associated tissues. As will be described below, cylindrical support 46, when combined with limited angles of gantry rotation, can effectively protect the bones and muscles of patient's arm and shoulder from radiation.

FIGS. 3 and 4 are plane views of exemplary barriers 26 in accordance with an embodiment of the present invention. In a specific embodiment shown in FIG. 3, barrier 26 is designed to have openings 30 and 42 adapted to allow patient's left breast and left arm passing therethrough. In another specific embodiment shown in FIG. 4, barrier 26 is designed to have openings 30 and 42 adapted to allow patient's right breast and right arm passing therethrough.

In some embodiments, barrier 26 can be divided into a first inner section 50 and a second outer section 52 by dotted line 54 as shown in FIGS. 3 and 4. Second outer section 52 can be mounted to the ceiling and the floor of the treatment room in which system 10 is installed. In a specific embodiment, first inner section 50 with openings can be detachable from second outer section 52 and replaceable. Thus, the size of opening 30 in first inner section 50 can be chosen to adapt to various size of patients' breasts. In another specific embodiment, first inner section 50 is rotatable with respect to second outer section 52 along dotted line 54. For example, first inner section 50 can be rotated counterclockwise to a position shown in FIG. 3 suitable for use in irradiating patient's left breast. Conversely, first inner section 50 can be rotated clockwise to a position shown in FIG. 4 suitable for use in irradiating patient's right breast.

In some embodiments, a slot 56 is provided between openings 30 and 42. Slot 56 is sized and shaped such that the soft tissue leading from breast 20 to the arm pit (axillary extension of the breast) extends therethrough to be exposed to radiation beam 18. This allows irradiation and imaging of the soft tissue leading from an uncompressed breast to the armpit. It is advantageous to image both the breast and its axillary extension since primary breast lesions often spread to infect lymph nodes in this region.

In some embodiments, barrier 26 can be provided with two arm openings adapted to sequentially allow each of the two arms passing through. For instance, one of the two arm openings is adapted to allow the left arm passing through when the patient's left breast is extended through opening 30 and exposed to radiation beam 18. Another arm opening is adapted to allow the patient's right arm passing through when the patient's right breast is extended through the same opening 30 and exposed to radiation beam 18. In these embodiments, each of the patient's breasts can be sequentially irradiated without the need of rotating first inner section 50 or modifying barrier 26.

Figure 8:
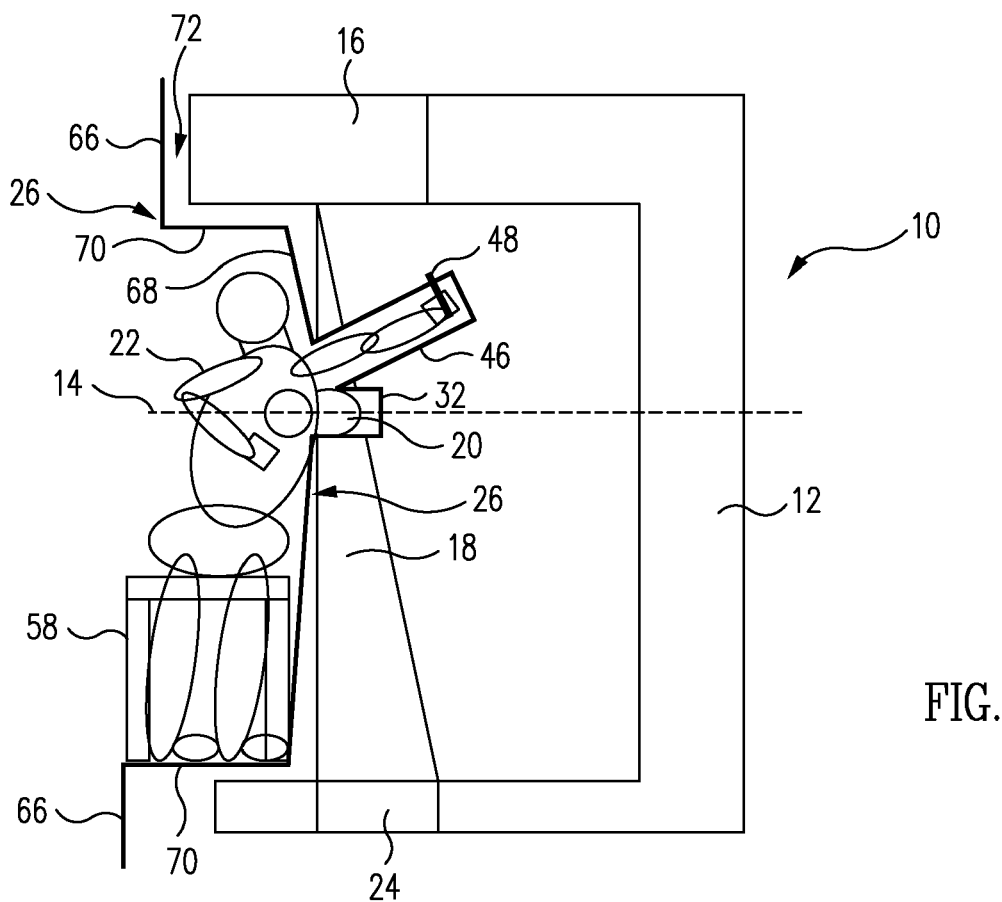
FIG. 8 schematically illustrates a radiation system including a barrier near a patient in accordance with another embodiment of the present invention.

Referring to FIG. 8, there is shown a barrier 26 in accordance with another embodiment of the present invention. In general, barrier 26 in FIG. 8 comprises a structure in a-convex shape and configured to be positioned near gantry 12, which is generally in a concave shape. Barrier 26 comprises a ledge portion 66, a main portion 68, and a band portion 70 connecting the ledge and main portions 66 and 68. An L-shaped region 72 is formed between ledge and band portions 66 and 70 and is configured to surround the outer perimeter of gantry 12. Main portion 68 is configured to be positioned in the gantry housing and adapted to support patient's body 22. Openings are provided in main portion 68 for a breast passing therethrough for irradiation. A stool 58 can be coupled to band portion 70 on which patient 22 can sit during imaging. In some embodiments, ledge 66, band 72 and main 68 portions are coupled together by conventional means such as by using bolts and nuts or by welding, etc. In some embodiments, the ledge, band and main portions are an integral unit. In one embodiment, stool 58 is an integral portion of barrier 26.

When barrier 26 is positioned near gantry 12, for example, being mounted to the ceiling and floor of the treatment room, free space can be created between the L-shape region and the ceiling and floor. Gantry 12 can freely rotate in the free space without collision with barrier 26 and patient's body 22. One of the advantages of barrier 26 in FIG. 8 is that the patient can be positioned further inside rotating gantry 12 so that irradiation beam 18 can be projected onto the breast and/or its axillary extension and/or its chest wall without the need to modify most standard gantries, which typically have radiation sources located in the central region of the source enclosure. Thus, the use of barrier 26 can eliminate the need to move radiation source 16 to the perimeter edge of gantry 12.

Figure 9:
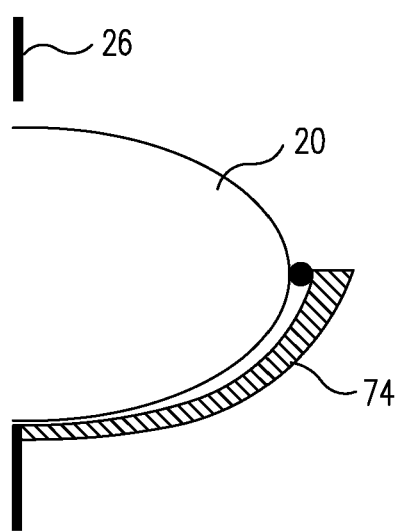
FIG. 9 schematically illustrates an uncompressed breast extended through an opening in a barrier and supported in a holder having a surface conformal to a portion of the breast in accordance with another embodiment of the present invention.

Referring to FIG. 9, there is shown a breast support 74 in accordance with another embodiment of the present invention. In comparison with the breast holder 32 shown in FIG. 2 which comprises a sealed hollow cylinder having an evacuating means, support 74 in FIG. 9 comprises an open ledge that supports the breast 20 from underneath. Support 74 can comprise a flat plate oriented horizontally or at some small angle (e.g. 5 to 30 degrees) to a horizontal axis. In some embodiments, support 74 can comprise a curved surface to conform to the form of an uncompressed breast. In some embodiments, support 74 comprises a combination of flat and curved surfaces. In some embodiments, support 74 comprises a flexible material that provides positioning and immobilization for the breast, such as like a bra.

In operation, in one embodiment, patient 22 sits on a stool 58, or alternatively, stands in front of barrier 26 in a substantially upright position. Alternatively stool 58 can be incorporated in barrier 26. Patient 22 rests against and is supported by barrier 26 and extends a breast 20 (e.g., the left breast as in FIG. 1) through an opening 30 in barrier 26 to be exposed to radiation beam 18. A radiation technician may assist in placing and positioning the breast 20 in holder 32 or support ledge 74. A vacuum pump (not shown) is turned on to provide vacuum so that the breast 20 is more completely drawn into and stabilized in holder 32. Patient 22 can also extend an arm (e.g., the left arm) through an opening 42 and grasp a hand bar 48 to rest the arm in support cylinder 46. Soft tissue leading from breast 20 to axilla extends through slot 56 to be exposed to radiation beam 18. An uncompressed breast 20 and soft tissue leading from the breast to axilla are thus ready for irradiation and imaging. Contrast agents can be optionally injected into uncompressed breast 20 to facilitate assessing suspicious lesions.

Radiation source 16 generates radiation beam 18 such as a cone x-ray beam. The cone x-ray beam can be at any x-ray energy level from kilovoltages (KeV) to megavoltages (MeV). For example, the cone x-ray beam generated by radiation source 16 can be at an energy level in the range from about 50 kVp to about 30 MV. In one embodiment, the cone x-ray beam can be at an energy level in the range from about 200 kVp to about 1000 kVp. In an embodiment shown in FIG. 5, radiation source 16 includes two x-ray beam generators: a kilovoltage x-ray beam generator 16a and a megavoltage x-ray beam generator 16b. Each of the two x-ray beam generators 16a and 16b is provided with a flat plate sensor 24a and 24b. In one embodiment, the pair of kilovoltage x-ray beam generator 16a and flat panel sensor 24a are mounted at 90 degrees to the pair of megavoltage x-ray beam generator 16b and flat plate sensor 24b in gantry 12. This configuration produces both a kilovoltage x-ray beam and a megavoltage x-ray beam 18a and 18b. In one embodiment, generator 16a generates a cone x-ray beam 18a at an energy level of approximately 125 kVp for diagnostic imaging of a breast and its axillary extension and chest wall. In another embodiment, generator 16b generates a cone x-ray beam 18b at an energy level of approximately 1-2 MV for radiotherapy and for diagnostic imaging with reduced ray and ring artifacts. As gantry 12 rotates around an axis such as a horizontal axis 14, projection and CT images, for diagnosis, staging, treatment planning, treatment targeting, and motion management, can be generated at kilovoltage and/or megavoltage energies and be immediately followed by radiation therapy at megavoltage energies.

Radiation beam 18 generated by radiation source 16 impinges on a dense x-ray absorbing block 28 shown in FIG. 6 to provide an x-ray beam with a specific shape, size, intensity, and direction of x-ray beam 18. In a specific embodiment shown in FIG. 6, a multileaf collimator 28 is disposed in front of radiation source 16 to produce a half cone x-ray beam with a sharp vertical edge 60 and semi-circular cross-section 62. Half cone beam with sharp vertical edge 60 is advantageous in reducing radiation dose to tissues of healthy body parts near the breast 20. The multileaf collimator 28 can be adjusted to other advantageous shapes, other than a flat boundary, such as a curved or bumpy surface of the lungs, so that the latter is better protected from the x-ray beam.

Gantry 12 rotates about an axis 14 such as a horizontal axis as controlled by a control module (not shown). As gantry 12 rotates, radiation beam 18 generated by radiation source 16 is projected onto breast 20 and its axillary extension from different directions. By way of example, cone x-ray beam is generated from radiation source 16 and projected onto breast 20 and soft tissue. Gantry 12 rotates 360 degrees or alternatively slightly more than 360 degrees (e.g. approximately 370 degrees) and approximately 500 to 600 projection images are taken at equally spaced angles to provide a complete set of projection data. Gantry 12 can also tilt from its horizontal position and rotates about an axis having an angle with horizontal axis 14 from about 0 to 85 degrees so that radiation beam 18 is projected to breast 20 from various angles. In some embodiments, gantry 12 rotates 180 degree plus the cone beam angle in a way that radiation beam 18 does not first pass through patient's shoulder and arm region prior to entering the breast area, to reduce radiation dose to healthy arm and shoulder tissue and bone volume. The portion of cylindrical support 46, through which no direct radiation beams pass on the way to the breast 20 and detector 24, can be made of a radiation absorbing material to protect patient 22 from scatter radiation exposure.

Detector 24 detects the radiation beam transmitted through breast 20 and produces radiation transmission data representing the intensity of the radiation transmitted through breast 20. An image processor (not shown) receives the transmission data from detector 24 and produces a plurality of single projection images, typically 500 to 600, that are then reconstructed into three-dimensional CT image data sets of breast 20, using reconstruction algorithms known in the art such as the Feldkamp algorithm.

After one breast (e.g., the left breast) is irradiated, the other breast (e.g., the right breast) can be exposed to radiation beam for imaging. This can be done by detaching first inner section 50 of barrier 26 and replacing with another inner section having openings designed for the right breast. Alternatively, inner section 50 is rotated clockwise to a position suitable for the right breast and right arm extending through the openings. In some embodiments, patient 22 can reposition herself to extend her right breast and right arm through the openings in barrier 26.

In another aspect of the invention for radiation therapy, both a kilovoltage x-ray source 16a and detector 24a and a megavoltage x-ray source 16b and detector 24b can be mounted onto a rotating gantry 12 and oriented at 90 degrees to each other as shown in FIG. 5. In some embodiments, the orientation of the axis of rotation 14 is horizontal where FIG. 5 is a front view and the patient's 22 head-to foot-orientation is substantially vertical. In some embodiments, patient 22 lies in a prone or supine position and gantry 12 rotates about a vertical rotation axis 14 under patient 22. In such embodiments, FIG. 5 is a top view and the patient's 22 head-to-foot orientation is substantially horizontal. In some embodiments, patient 22 lies in a supine position and gantry 12 can be suspended above patient 22 and rotates about a vertical axis of rotation 14. In such embodiments, FIG. 5 is a bottom view and the patient's 22 head-to-foot orientation is substantially horizontal. In some embodiments, the patient's head-to-foot orientation can be in any plane from vertical to horizontal, or stated alternatively, the angle between patient's head-to-foot orientation and a vertical axis can be at any desired angle.

Gantry 12 is rotated with the kilovoltage source 16a on to acquire a complete kilovoltage cone beam CT data set. This can be a complete 360 rotation. In some embodiments, gantry 12 rotates 180 degrees plus the cone beam angle (e.g., 20 to 30 degrees) so that the kilovoltage x-rays do not pass first through the shoulder and arm of patient 22.

In another aspect of this invention, the arm support structure (including a cylindrical tube and/or curved tube-like structure or a combination of the two) contains radiation absorbing material or materials to reduce the radiation dose to healthy tissues of the inserted shoulder and arm or to parts of them.

The kilovoltage x-ray source 16a can be configured to have its beam emerge from the boundary edge of gantry 12 near patient 22 as shown in FIG. 1. The kilovoltage source beam 18a can be shaped with an x-ray absorbing block 28 as shown in FIG. 6, to provide a half cone shape 62 as shown in FIG. 7. This allows the incident kilovoltage beam 18a to pass through the muscle of the patient's 22 chest wall with minimal exposure to the head and neck, the heart and lungs, and the other healthy parts of the patient's body 22.

Barrier 26 can be configured to block kilovoltage x-ray beam 18a or its scattered components that do not travel directly from source 16a to kilovoltage detector 24a and pass through the breast 20 or its axillary extension toward the arm pit. Barrier 26 can also be configured to transmit kilovoltage X-rays 18a that pass through the muscle of the chest wall adjacent to the breast 20. As described above, the breast 20 is placed into hollow cylinder 32 for stable positioning and support. An end cap 34 and vacuum line 38 can be attached to hollow cylinder 32 to assist in obtaining proper placement of the breast 20 relative to the kilovoltage x-ray beam source 16a and detector 24a.

The megavoltage x-ray beam source 16b can be more centrally located from the boundary of gantry 12. In some embodiments, beam source 16b can be positioned by gantry 12 to several (e.g., 2 to 8) angles and orientations to deliver a proscribed megavoltage dose to the breast 20, its axillary extension toward the arm pit, and the muscle wall of the chest adjacent to the breast 20 and avoid a large dose delivery to other sensitive areas, such as the head, neck, heart and lungs of the patient 22. Selection of such specific megavoltage orientations and angles is well known to radiation oncology practitioners and has been described by S. V. Formenti et al. in *International Journal of Radiation Oncology, Biology, and Physics*, Vol. 60, 2004, pp. 493-504.

The location, extent, shape, orientation and/or boundaries of the malignant tumor are precisely determined in three dimensional space, relative to the gantry 12 system coordinate, by the kilovoltage source 16a and detector's 24a acquisition of a cone beam CT data set. These data are analyzed to either compare these specifications to a preexisting treatment plan or to produce a new or a modified treatment plan. Then a desired dose, to the whole breast 20 and/or its axillary extension and/or its adjacent chest wall muscle, or to a restricted volume containing the malignant tumor, is accurately delivered by megavoltage source 16b, monitored by detector 24b such as a flat panel megavoltage sensor, all on the single gantry 12 and all during a short time span (e.g., less than 30 minutes) for a single dose delivery. Since megavoltage x-ray beam radiotherapy is routinely administered in many separate daily doses, called fractions, over many weeks, this type of monitoring allows some determination of the tumor's response to treatment. This response can be indicated by comparisons to earlier fractions, as evident by changes in location, extent, shape, orientation, boundaries, or by detection of contrast agents related to functional, biological and/or structural characteristics, where these agents are administered as a part of the treatment setup and delivery, and the evaluation is from cone beam CT data set viewing and analysis procedures. The time response of contrast agent uptake and flush out contributes medically relevant information on the properties and characteristics of the cancer lesions and their surrounding tissues. The three dimensional CT data sets can be extended to the $4^{th}$ dimension of time by using respiratory gating during the cone beam CT acquisition to correlate position with the phase of the patient's 22 breathing process.

Figure 10:
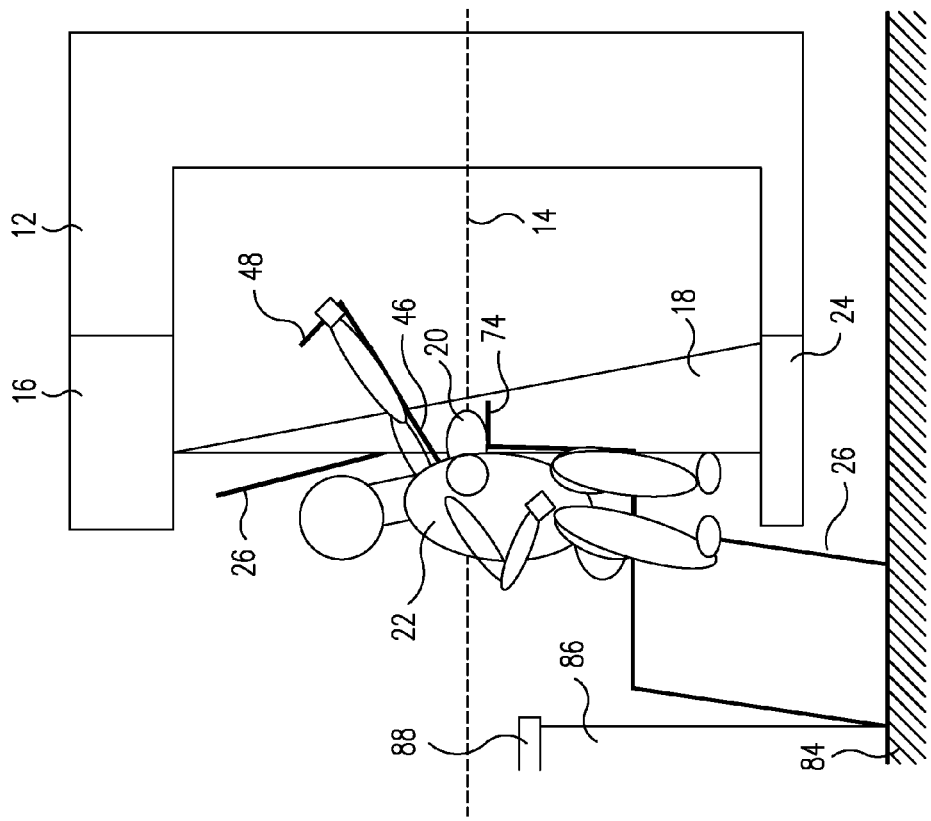
FIG. 10 is a side view illustrating a radiation system including an adjustable barrier in accordance with an embodiment of the present invention.
Figure 11:
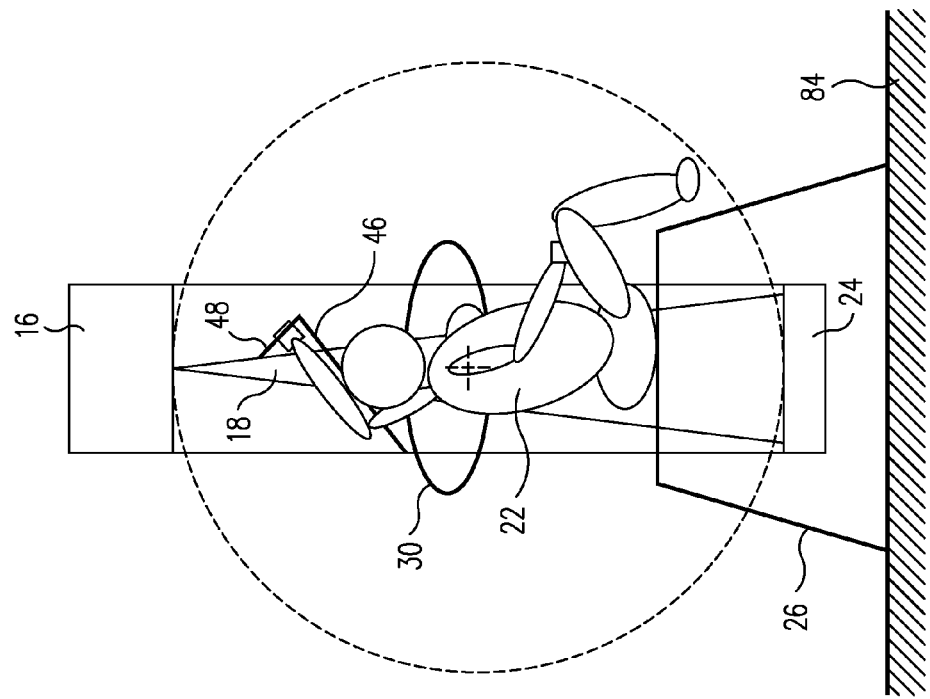
FIG. 11 is a front view illustrating a radiation system including an adjustable barrier in accordance with an embodiment of the present invention.

FIGS. 10-11 illustrate another embodiment of barrier 26, which is adjustable to adapt to various positions of patient's body 22. In this embodiment, the material forming barrier 26 is selected such that barrier 26 is bendable arid/or adjustable to adapt to a desired position of patient 22 when in use. The adjustable barrier 26 is sufficiently robust to support patient's body 22 leaning against the barrier. Suitable materials for forming adjustable barrier 26 include but are not limited to aluminum.

In some embodiments, adjustable barrier 26 is in the form of a skeletal frame that includes a minimum number of components needed to support or position patient 22 in a desired position. In general, a skeletal frame comprises a minimalist structure that provides support and/or positioning of the patient and/or other structures such as positioning devices and radiation barriers. Suitable materials for constructing a skeletal frame include aluminum, stainless steel, chrome molly steel, fiberglass, plastics, and carbon fiber materials and composites. A skeletal frame may optionally incorporate some positioning and shielding if desired. Lead lined curtain and/or cushion pad may be attached to the skeletal frame. As one example, when barrier 26 in form of a skeleton frame is in use, patient 22 may wear a lead lined uniform such as a lead lined hospital gown that opens in the back or a lead lined gown shirt and apron to protect other healthy body parts from unnecessary irradiation. A separate, flexible lead lined sleeve can be placed around patient's hand, and part of the arm to provide further protection. If desired, a shin guard plate can be attached to the frame near floor 84 of the treatment room to protect any body parts exposed below the bottom of the gown or apron. One of advantages of barrier 26 shown in FIGS. 10-11 is that it can be made compact and easily installed by, for example, bolts and nuts in the treatment room and conveniently removed. Alternatively, the system may be made such that it may be positioned relative to an imaging or treatment system without attachment, by for example, having some type of mating registration points that fit securely onto a portion of the imaging or treatment system. For example, barrier 26 can be installed between a gantry 12 and a couch 86 of an existing cone beam CT system without any major modification of the system. After patient's breasts are imaged and/or treated, barrier 26 is removed so that the CT system can perform imaging and/or treatment of other body parts of a patient. For instance, a patient can now lie on a couch top 88, which can be moved into gantry 12 after the barrier 26 is removed.

FIGS. 12-16 illustrate further embodiments of the present invention in which patient 22 can sit or lie side ways on couch top 88 during imaging and/or treatment. Barrier 26 is coupled to an end or other location of couch top 88 and configured to support and protect patient 22. While not shown in FIGS. 12-16, couch 86 may include a moveable portion (not shown) driven by a moving mechanism such as precision motors. The moveable potion can be translated in three directions (x, y, and z). Couch 86 may be provided with a titling mechanism for titling the moveable portion with respect to the x-y plane. Couch top 88 is coupled to the moveable portion and can be translated and/or titled with the couch's moveable portion. Couch top 88 can also be moved independent of the moveable portion. For example, couch top 88 can be independently translated in x-direction to move patient 22 into and out of gantry 12.

Figure 15:
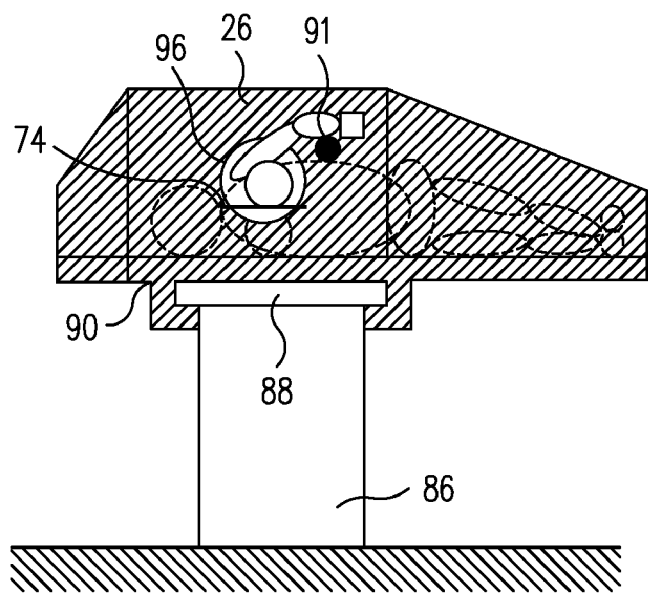
FIG. 15 is a side view illustrating a moveable support attachment supporting a patient in a lying position in accordance with an embodiment of the present invention.
Figure 16:
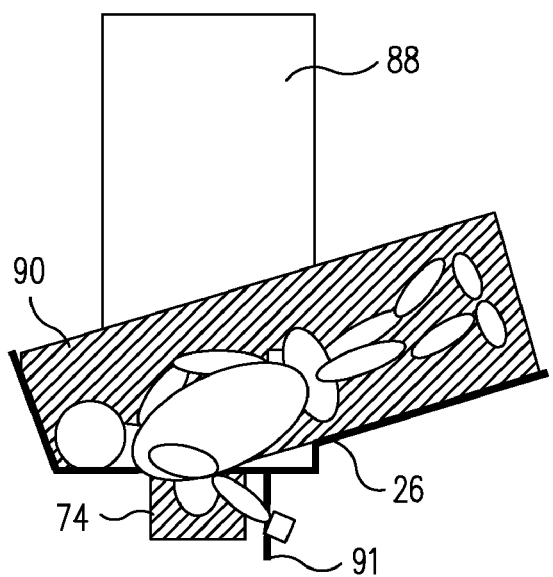
FIG. 16 is a top view illustrating a moveable support attachment supporting a patient in a lying position in accordance with an embodiment of the present invention.

A support attachment 90 can be coupled to and moved with couch top 88. By way of example, support attachment 90 can be an aluminum frame secured to couch top 88. Support attachment 90 can be secured to couch top 88 by various means known in the art. For example, support attachment 90 can be hooked to couch top 88 at one end so that it can be conveniently removed after imaging and/or treatment of patient's breast. Support attachment 90 can be moved together with couch top 88. For example, support attachment 90 can be translated in three dimensions and tilted. In some embodiments, support attachment 90 can be moved independent of couch top 88. As shown in FIGS. 15-16, support attachment 90 can be rotated in the plane of couch top 88.

While support attachment 90 is illustrated and described with embodiments of an existing imaging system including a moveable couch top, it will be appreciated that support attachment 90 can be used in designing a mammography CT system. In such a mammography CT system, support attachment 90 may be coupled to a couch base, which can be provided with a moving mechanism capable of translating, tilting, and/or rotating support attachment 90.

Barrier 26 such as an adjustable support illustrated in FIGS. 10-11 can be coupled to support attachment 90 at one end by various means known in the art. Barrier 26 can be in the form of a skeleton frame consisting of a minimum number of parts needed to support patient 22. A skeletal frame 26 may optionally incorporate some positioning and shielding if desired. As one example, a leaded curtain can be placed on the skeleton frame to block any unnecessary radiation of patient's healthy body parts. A thin metal sheet such as aluminum sheet can also be used. Alternatively, patient 22 may wear a leaded uniform such as a lead lined hospital gown that opens in the back or a lead lined gown shirt and apron to protect other healthy body parts. Openings are provided in the leaded curtain and/or metal sheet to allow patient's breast and its axillary extension passing through.

Figure 13:
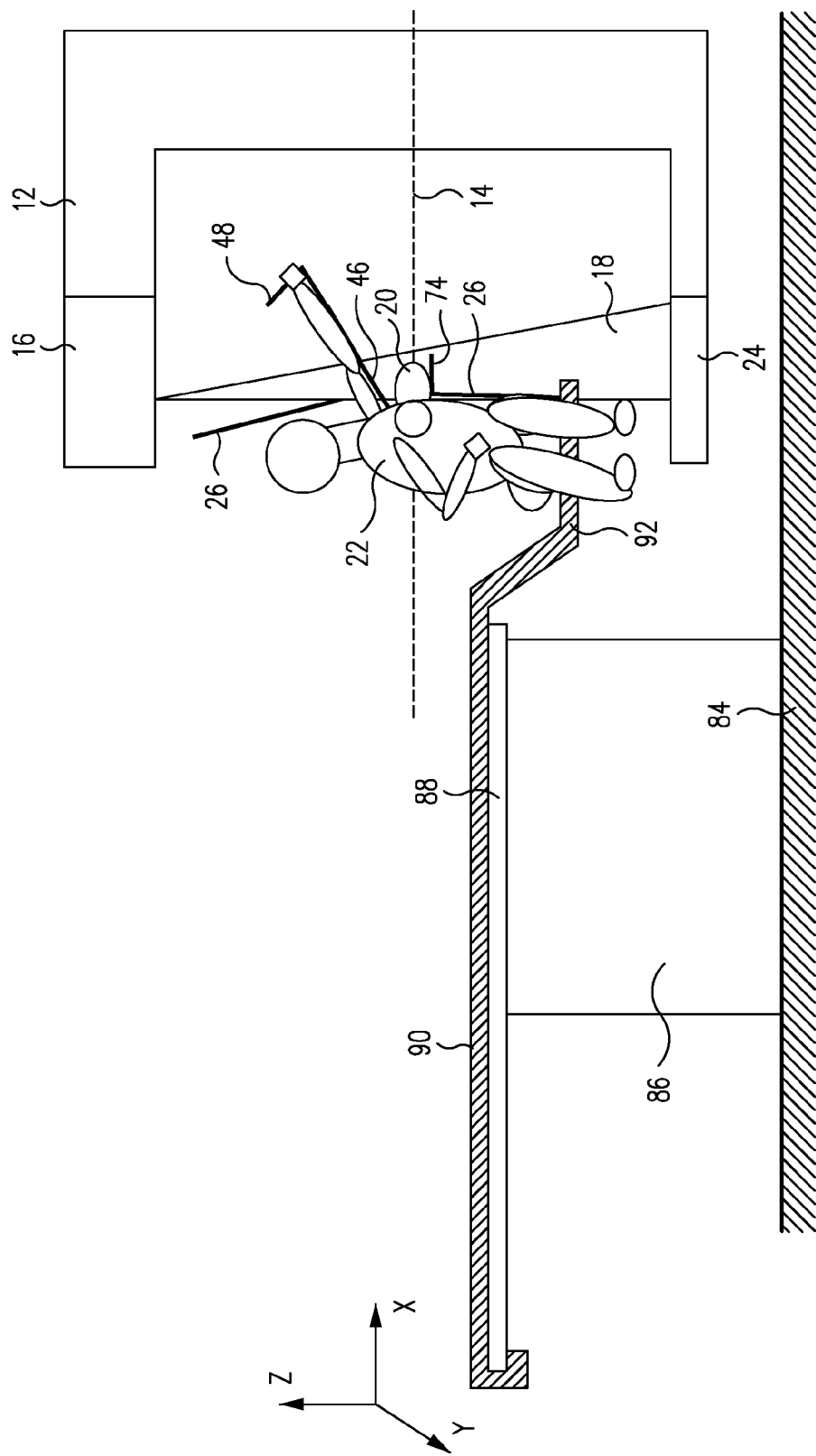
FIG. 13 schematically illustrates a radiation system including a barrier coupled to a moveable couch top in accordance with another embodiment of the present invention.

FIG. 13 illustrates an embodiment of the present invention in which a portion such as one end of support attachment 90 is configured to adapt to patient's body build. As shown, support attachment 90 may include a drop-down portion 92 at one end to adapt to tall patients. Drop-down portion 92 is desirable for tall patients in aligning their breasts and/or axillary extension with the gantry's rotation axis 14. Alternatively, support attachment 90 may include a raise-up portion (not shown) to adapt to short patients in aligning their breasts with gantry's rotation axis 14.

FIGS. 15-16 illustrate an embodiment of the present invention in which patient 22 may lie on her side on a support attachment 90 during imaging and/or treatment. As shown, support attachment 90 is coupled to couch top 88 at an angle that allows patient 22 to lie on her side without major body contortion. Barrier 26 is coupled to support attachment 90 and provided with an opening 96 that allows breast 20, its axillary extension, and optionally an arm passing through. Breast 20 is supported on support ledge 74 and exposed to a radiation beam. Support 91 is provided to secure and support barrier 26. This embodiment greatly reduces body contortion and provides greater comfort for patients 22. In an embodiment, support attachment 90 can be rotated in the plane of couch top 88, independent of the movement of couch top 88. In another embodiment, barrier 26 is an integral portion of support attachment 90 and moveable during patient positioning.

Figure 17:
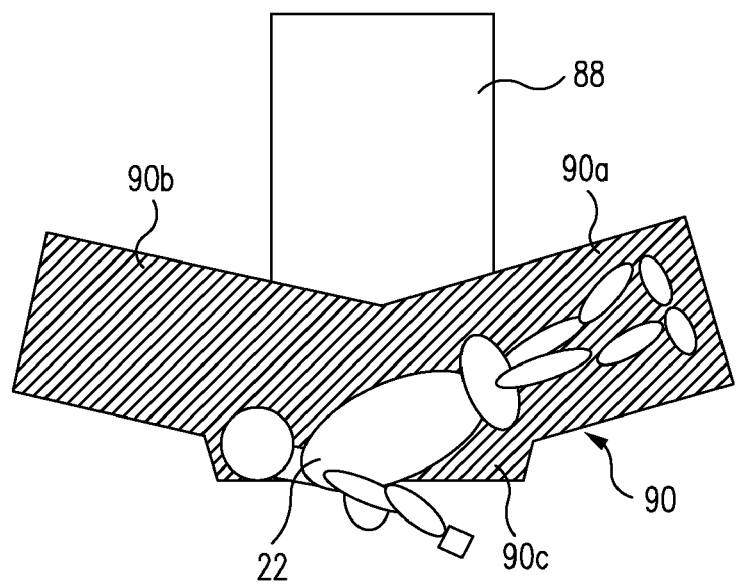
FIG. 17 schematically illustrates a support attachment which comprises two wing portions adapted to support a patient in a lying position from either side in accordance with an embodiment of the present invention.

FIG. 17 illustrates another embodiment of support attachment 90, which is adapted to allow patient 22 to lie down from either side so that both breasts and their associated tissues can be easily imaged. As shown, support attachment 90 can be in Y- or V-shape having two wing portions 90a and 90b and a central portion 90c. Two wing portions 90a and 90b may be angled such that patient 22 can lie down comfortably on her side on either wing portion without major body contortion. Barrier 26 (not shown in FIG. 17) can be coupled to central portion 90c.

Figure 18:
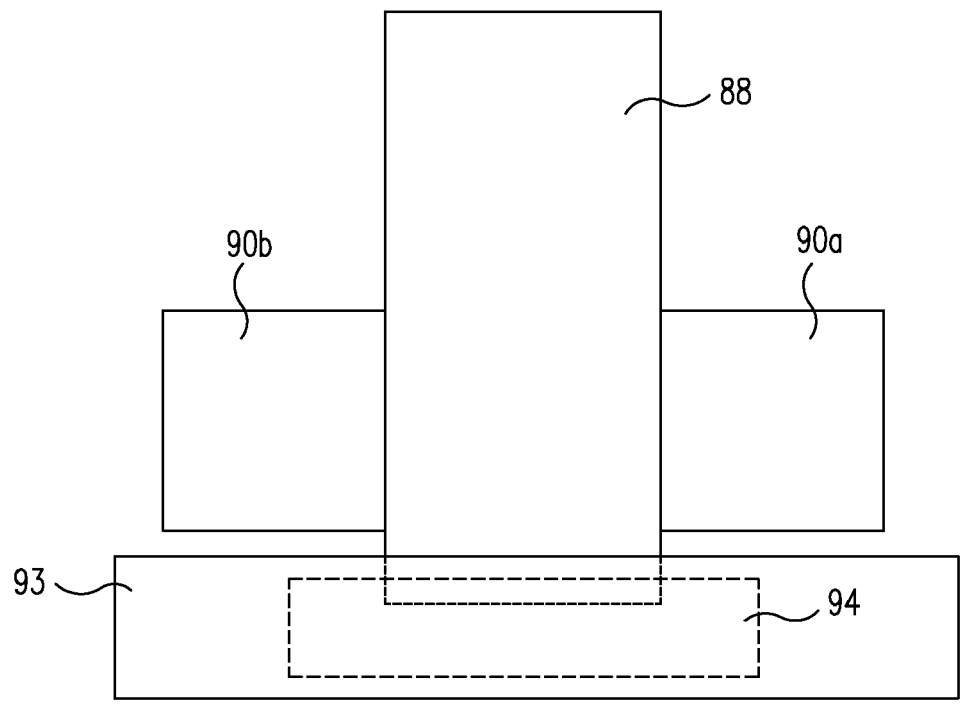
FIG. 18 schematically illustrates a support attachment which comprises two attachable and/or foldable wing portions in accordance with an embodiment of the present invention.

FIG. 18 illustrates another embodiment of support attachment 90, which comprises two attachable and/or foldable wing portions 90a and 90b. Various mechanisms known in the art such as slides and brackets can be used to attach and/or fold wing portions 90a and 90b. In one embodiment, wing portions 90a and 90b are attachable to couch top 88 and foldable against couch 86. In such embodiment, wing portions 90a and 90b are moveable with couch top 88. In another embodiment, wing portions 90a and 90b can be coupled to a gantry housing 93 such as of a ring gantry CT system. There exists a need for very fast cone beam CT of breasts. For instance, when X-ray contrast agents are injected into the blood stream, it is desirable that the transport of the contrast agents with time is imaged so that more precise information can be obtained on the target lesion or lesions and their response to treatments, like external beam radiotherapy. In an enclosed gantry CT, the rotation speed can be on the order of 0.3 to 0.4 seconds per rotation. At such high rotation speeds, an enclosed gantry is desired for safety. FIG. 18 schematically shows an enclosed ring gantry CT system having a cylindrical tunnel opening 94. When wing portions 90a and 90b are attached to gantry housing 93, couch top 88 can freely move in and out opening 94, independent of the side wing portions 90a and 90b attached to gantry housing 93.

In use, patient 22 sits on e.g. one end of support attachment 90 and leans against barrier or support frame 26 as shown in FIGS. 12-13. Alternatively, patient 22 may lie on her side on support attachment 90 as illustrated in FIGS. 15-18. Patient 22 is positioned such that a breast and/or its axillary extension extend through the opening(s) provided in barrier 26 and are supported in breast support 32 or 74. The couch's moveable portion and/or couch top move patient 22 into gantry 12 at a position that exposes the patient's breast and/or its axillary extension to radiation beam 18. The elevation (z-direction) of the couch's moveable portion is adjusted such that the patient's breast and/or its axillary extension substantially align with the axis of rotation 14 of gantry 12. Couch top 88 can also be adjusted by the tilting mechanism provided in couch 86. Support attachment 90 may also be rotated during the adjustment.

Figure 14:
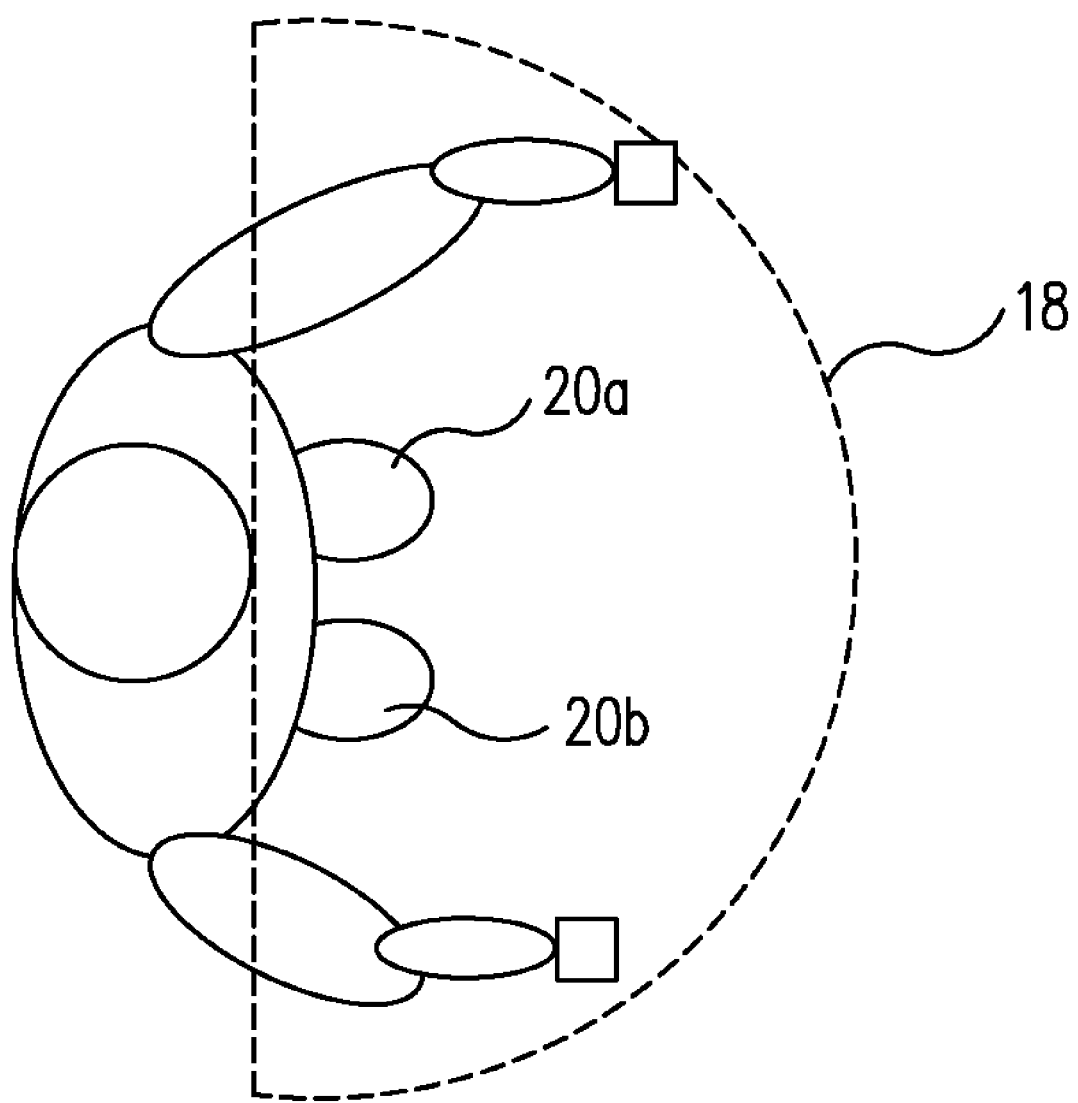
FIG. 14 schematically illustrates simultaneous irradiation of both breasts of a patient in accordance with an embodiment of the present invention.

The above various embodiments of the present invention are described in the context where one breast is imaged and/or treated at one time. It should be pointed out that if both breasts need to be imaged and/or treated, both breasts 20a and 20b and their axillary extension can be simultaneously irradiated, as illustrated in FIG. 14. This can be achieved by providing, for example, two openings in barrier 26 to allow both breasts and/or their axillary extension passing through. One advantage of irradiating both breasts simultaneously is that it can not only save time but also reduce radiation doses to patients.

The present invention provides a system and method for providing three-dimensional computed tomography and radiotherapy of tumorous tissues in patient's uncompressed breasts. This eliminates the pain suffered by patients in conventional mammography during which the breasts are compressed. Contrast agents circulate more effectively in uncompressed breasts and can be advantageously used in the present invention to facilitate assessing suspicious lesions. Another advantage of the present invention is that not only the breasts themselves, but also the soft tissues leading from the breasts to the axilla (arm pit) and the muscle of the chest wall, can be irradiated and examined, while the radiation dose to healthy heart, lung, and other body part tissues is minimized. Moreover, the present system and method can make immediate use of widely available CT gantry systems and external beam radiotherapy systems, which primarily have axes of rotation that are horizontal. The clear position, shape and volume information on any malignant lesions from the breast through the axilla can be coupled to a system for efficient and prompt radiotherapy via external beam radiotherapy and/or brachytherapy.

The foregoing description of specific embodiments and examples of the invention have been presented for the purpose of illustration and description, and although the invention has been described and illustrated by certain of the preceding examples, it is not to be construed as being limited thereby. They are not intended to be exhaustive or to limit the invention to the precise forms disclosed, and many modifications, improvements and variations within the scope of the invention are possible in light of the above teaching. It is intended that the scope of the invention encompass the generic area as herein disclosed, and by the claims appended hereto and their equivalents.

The invention claimed is:

1. A structure for use in irradiating a portion of a body, said structure being adapted to be positioned adjacent to a gantry which is rotatable about a horizontal axis and comprises a radiation source for generating a radiation beam and a detector spaced from the radiation source and being adapted to be positioned between the body and at least a portion of the radiation beam and being provided with an opening adapted to allow a portion of the body passing therethrough to be exposed to the radiation beam, said structure comprising a holder for supporting the portion of the body, said holder being substantially cylindrical, and comprising an end cap that is removable for facilitating positioning of a breast in the holder and means for evacuating the holder.

2. The structure of claim 1, which comprises an first area proximate the opening and encompassing an additional portion of the body proximate the portion of the body, and a second area, said first area transmitting radiation to a greater extent than said second area.

3. The structure of claim 1, wherein the opening is configured to include a first portion adapted to allow the breast and a second portion adapted to allow tissue between the breast and an arm pit passing therethrough to be exposed to the radiation beam.

4. The structure of claim 1, which further comprises a gasket for sealing the breast in the holder.

5. The structure of claim 1, which further comprises a panic button coupled to the evacuating means.

6. The structure of claim 1, which is further provided with a plurality of holes surrounding the opening for preventing formation of vacuum in a region beyond the portion of the body.

7. The structure of claim 1, which is further provided with an additional opening adapted to allow an arm of the patient passing therethrough.

8. The structure of claim 1, which is in the shape of a cone, partial spheroid, or pyramid.

9. The structure of claim 1, wherein a portion of the structure including the opening protrudes inward of the gantry such that the portion of the body is positioned for irradiation by the radiation source disposed a distance from an edge of the gantry.

10. The structure of claim 1, which is adjustable to adapt to a desired position of the patient.

11. The structure of claim 10, which is in the form of a skeleton frame.

12. The structure of claim 1 wherein the structure is provided with the opening to allow a breast of a patient passing therethrough, and is adapted to support at least a portion of the rest of the patient's body.

13. The structure of claim 1 wherein the structure is provided with the opening to allow a breast of a patient passing therethrough, and is adapted to cause at least some portion of the patient's body to receive less radiation than the breast.

14. A structure for use in irradiating a portion of a body, said structure being adapted to be positioned adjacent to a gantry which is rotatable about a horizontal axis and comprises a radiation source for generating a radiation beam and a detector spaced from the radiation source and being adapted to be positioned between the body and at least a portion of the radiation beam and being provided with an opening adapted to allow a portion of the body passing therethrough to be exposed to the radiation beam,
wherein the structure comprises an inner section and an outer section, said inner section is detachable from the outer section and provided with the opening.

15. The structure of claim 14 wherein the inner section is rotatable with respect to the outer section such that the location of the opening in the barrier is changeable.

16. A structure for use in irradiating a breast of a patient in a gantry which comprises a radiation source for generating a radiation beam and a detector spaced from the radiation source,
said structure being adapted to be positioned between the patient and the gantry and being provided with a first opening adapted to allow the breast passing therethrough to be exposed to the radiation beam and a second opening adapted to allow tissue between the breast and an arm pit passing therethrough to be exposed to the radiation beam, said second opening extending from said first opening.

17. The structure of claim 16, which comprises an first area proximate the opening and encompassing an additional portion of the body proximate the portion of the body, and a second area, said first area transmitting radiation to a greater extent than said second area.

18. The structure of claim 16, wherein the structure includes the first opening adapted to allow the breast passing therethrough to be exposed to the radiation beam, a third opening adapted to allow an arm passing therethrough, and the second opening connecting the first and third openings adapted to allow the tissue between the breast and arm pit passing therethrough to be exposed to the radiation beam.

19. The structure of claim 16 wherein the second opening is a slot extending from the first opening to a location corresponding to an armpit region.

20. A method of irradiating a portion of a body, comprising the steps of:
providing a gantry, said gantry comprising a radiation source for generating a radiation beam and a detector spaced from the radiation source;
providing a structure near the body, said structure provided with an opening adapted to allow a portion of the body passing therethrough;
extending a portion of the body through the opening in the structure to expose the portion to the radiation beam;
rotating the gantry about a horizontal axis, whereby the portion of the body is irradiated by the radiation beam and detected by the detector;
wherein said opening includes a first portion adapted to allow a breast of a patient passing therethrough and a second portion adapted to allow tissue between the breast and an arm pit passing therethrough, said second portion extending from said first portion, and wherein the extending step includes extending the breast and the tissue passing through the first and second portions to be exposed to the radiation beam.

21. The method of claim 20 wherein the portion of the body is a breast of a patient.

22. The method of claim 20,
wherein the structure is provided with an additional opening, and wherein the method further comprises the step of extending an arm of the patient through the additional opening in the structure.

23. The method of claim 22, wherein the step of rotating comprises rotating the gantry in 180 degrees plus a cone beam angle such that a majority of projections of the radiation beam do not traverse the patient's head and/or neck and/or arm prior to traversing the breast.

24. The method of claim 20 wherein the structure is provided with the opening to allow a breast of a patient passing therethrough, and is adapted to support at least a portion of the rest of the patient's body.

25. The method of claim 20 wherein the structure is provided with the opening to allow a breast of a patient passing therethrough, and is adapted to cause at least some portion of the patient's body to receive less radiation than the breast.

26. The method of claim 20 wherein the second portion is a slot extending from the first portion to a location corresponding to an armpit region.

27. A system for irradiating a breast of a patient, comprising:
a gantry comprising a radiation source for generating a radiation beam and a detector spaced from the radiation source; and
a structure positioned near the patient, said structure is provided with a first opening adapted to allow the breast passing therethrough to be exposed to the radiation beam and a second opening adapted to allow tissue between the breast and an arm pit passing therethrough to be exposed to the radiation beam, said second opening extending from said first opening.

28. The system of claim 27 wherein the gantry is rotatable about a horizontal axis, and said structure is adapted to support the patient's torso in a substantially upright position during irradiation.

29. The system of claim 27 wherein the structure includes the first opening adapted to allow the breast passing therethrough to be exposed to the radiation beam, a third opening adapted to allow an arm passing therethrough, and the second opening connecting the first and third openings adapted to allow the tissue between the breast and the arm pit passing therethrough to be exposed to the radiation beam.

30. The system of claim 27, wherein the structure comprises a first area proximate the opening and encompassing an additional portion of the body proximate the portion of the body, and a second area, said first area transmitting radiation to a greater extent than said second area.

31. The system of claim 27 wherein a portion of the structure including the opening protrudes inward of the gantry such that the body is inward of an outer reach of the gantry, and wherein the radiation source is disposed a distance from an edge of the gantry.

32. The system of claim 27, which further comprises a holder comprising a surface conformal to a portion of an uncompressed breast and supporting the breast from underneath.

33. The system of claim 27, wherein said radiation source comprises a first radiation source for generating a first radiation beam in a kilovoltage energy level and a second radiation source for generating a second radiation beam in a megavoltage energy level.

34. The system of claim 33 wherein said first and second radiation sources are attached to a common gantry.

35. The system of claim 33, wherein said first radiation source is attached to a first gantry, and said second radiation source is attached to a second gantry.

36. The system of claim 27 wherein the second opening is a slot extending from the first opening to a location corresponding to an armpit region.

37. A system for irradiating a breast of a patient, comprising:
a gantry comprising a radiation source for generating a radiation beam and a detector spaced from the radiation source;
a couch spaced from said gantry;
support attachment coupled to said couch;
a structure coupled to said couch, said structure being positioned near the patient, and provided with an opening adapted to allow a breast passing therethrough to be exposed to the radiation beam;
wherein said support attachment comprises two wing portions, each being adapted to support the patient in a lying position.

38. The system of claim 37 wherein said support attachment is moveable in three directions (x, y, and z).

39. The system of claim 37 wherein said support attachment is moveable independent of the couch.

40. The system of claim 37 wherein each of the two wing portions is attachable and/or foldable.

41. The system of claim 37 wherein the wing portions are coupled to a gantry housing.

42. A system for irradiating a breast of a patient, comprising:
a gantry comprising a radiation source for generating a radiation beam and a detector spaced from the radiation source;
a couch spaced from said gantry, said couch being adapted to support the patient's torso in a slant position relative to a horizontal plane during irradiation; and
a structure being adapted to be positioned near the patient, and provided with a first opening adapted to allow a breast passing therethrough to be exposed to the radiation beam, a second opening adapted to allow tissue between the breast and an arm pit passing therethrough to be exposed to the radiation beam, and a third opening adapted to allow an arm passing therethrough, and the second opening connecting the first and third openings, wherein the second opening is a slot extending from the first opening to the third opening.

43. An imaging system comprising:
a radiation source;
a detector spaced from the radiation source; and
a structure near the radiation source, said structure being provided with a first opening adapted to allow a breast and a second opening adapted to allow tissue between the breast and an arm pit of a patient passing therethrough to be exposed to at least a portion of a radiation beam generated by the radiation source, said second opening extending from said first opening.

44. The imaging system of claim 43 wherein the second opening is a slot extending from the first opening to a location corresponding to an armpit region.

45. A method of imaging comprising the steps of:
providing a system comprising a radiation source, a detector spaced from the radiation source, and a structure near the radiation source, said structure being provided with an opening adapted to allow a portion of a body passing therethrough;
positioning the body in a slant position relative to a horizontal plane;
exposing the portion of the body in the slant position to at least a portion of a radiation beam generated by the radiation source; and
obtaining one or more images of the portion of the body using the detector.

46. A method of imaging comprising the steps of:

providing a system comprising a radiation source, a detector spaced from the radiation source, and a structure near the radiation source, said structure being provided with a first opening adapted to allow a breast and a second opening adapted to allow tissue between the breast and an arm pit of a patient passing therethrough, said second opening extending from said first opening;

exposing the breast and the tissue to at least a portion of a radiation beam generated by the radiation source; and obtaining one or more images of the breast and the tissue using the detector.

* * * * *

UNITED STATES PATENT AND TRADEMARK OFFICE
CERTIFICATE OF CORRECTION

| | |
|---|---|
| PATENT NO. | : 7,492,858 B2 |
| APPLICATION NO. | : 11/134695 |
| DATED | : February 17, 2009 |
| INVENTOR(S) | : Partain et al. |

It is certified that error appears in the above-identified patent and that said Letters Patent is hereby corrected as shown below:

ON THE TITLE PAGE:

Bracketed number (75) for the second inventor David H. Humber: replace "Los Altos" with -- Los Gatos --.

IN THE SPECIFICATION:

Column 13, line 57, replace "arid/or" with -- and/or --.

Signed and Sealed this

Twelfth Day of May, 2009

JOHN DOLL
*Acting Director of the United States Patent and Trademark Office*